US011331411B2

(12) United States Patent
Stouthamer et al.

(10) Patent No.: US 11,331,411 B2
(45) Date of Patent: May 17, 2022

(54) RESORBABLE BIODEGRADABLE MEDICAL AND COSMETIC COMPOSITION COMPRISING POLY(1,3-TRIMETHYLENE CARBONATE)

(71) Applicant: AQPHA IP B.V., Utrecht (NL)

(72) Inventors: Jeffrey Markgregorius Maria Stouthamer, Utrecht (NL); Mónica Eunice dos Santos Rocha, Uithoorn (NL); Henderikus Supèr, Hardinxveld-Giessendam (NL); Alexius Josephus Lankhorst, Tiel (NL)

(73) Assignee: AQPHA IP B.V., Utrecht (NL)

( * ) Notice: Subject to any disclaimer, the term of this patent is extended or adjusted under 35 U.S.C. 154(b) by 130 days.

(21) Appl. No.: 16/618,167

(22) PCT Filed: May 30, 2018

(86) PCT No.: PCT/EP2018/064144
§ 371 (c)(1),
(2) Date: Nov. 29, 2019

(87) PCT Pub. No.: WO2018/219987
PCT Pub. Date: Dec. 6, 2018

(65) Prior Publication Data
US 2021/0138110 A1 May 13, 2021

(30) Foreign Application Priority Data
May 30, 2017 (EP) .................................. 17173563

(51) Int. Cl.
| | |
|---|---|
| *A61L 27/20* | (2006.01) |
| *A61P 15/10* | (2006.01) |
| *A61P 17/00* | (2006.01) |
| *A61P 19/02* | (2006.01) |
| *A61P 13/10* | (2006.01) |
| *A61P 1/04* | (2006.01) |
| *A61K 9/00* | (2006.01) |
| *A61L 27/58* | (2006.01) |
| *C08G 18/44* | (2006.01) |

(52) U.S. Cl.
CPC ............ *A61L 27/20* (2013.01); *A61K 9/0021* (2013.01); *A61L 27/58* (2013.01); *A61P 1/04* (2018.01); *A61P 13/10* (2018.01); *A61P 15/10* (2018.01); *A61P 17/00* (2018.01); *A61P 19/02* (2018.01); *C08G 18/44* (2013.01)

(58) Field of Classification Search
CPC .. A61L 27/20; A61L 27/58; A61P 1/04; A61P 13/10; A61P 15/10; A61P 17/00; A61P 19/02; A61K 9/0021; C08G 18/44
See application file for complete search history.

(56) References Cited

U.S. PATENT DOCUMENTS

| | | | | |
|---|---|---|---|---|
| 2002/0151466 | A1* | 10/2002 | Hubbard | ............... C04B 35/636 |
| | | | | 435/6.16 |
| 2003/0093157 | A1 | 5/2003 | Casares | |
| 2008/0107744 | A1 | 5/2008 | Chu | |
| 2008/0241072 | A1* | 10/2008 | Barry | ........................ A61P 1/04 |
| | | | | 424/9.36 |

FOREIGN PATENT DOCUMENTS

| | | |
|---|---|---|
| EP | 0711548 A1 | 5/1996 |
| WO | WO9856431 A1 | 12/1998 |
| WO | WO2009014441 A2 | 1/2009 |
| WO | WO2016074794 A1 | 5/2016 |
| WO | WO2017039435 A1 | 3/2017 |

OTHER PUBLICATIONS

Zhang et al., PTMC and MPEG-PTMC Microparticles for Hydrophilic Drug Delivery, Jan. 3, 2005, J. Control. Release, vol. 101, pp. 392-394. (Year: 2005).*
Wang, Frank, et al. "In vivo stimulation of de novo collagen production caused by cross-linked hyaluronic acid dermal filler injections in photodamaged human skin." Archives of dermatology 143.2 (2007): 155-163.
Medical Devices: Guidance document, Dec. 3, 2009. Retrieved from the Internet: URL:http://ec.europa.eu/health/medical -devices/files/meddev/2 1 3 rev 3-12 2009 en.pdf.
Mukherjee, Debi P., et al. "Effect of 3D-microstructure of bioabsorbable PGA: TMC scaffolds on the growth of chondrogenic cells." Journal of Biomedical Materials Research Part B: Applied Biomaterials: An Official Journal of The Society for Biomaterials, The Japanese Society for Biomaterials, and The Australian Society for Biomaterials and the Korean Society for Biomaterials 88.1 (2009): 92-102.
Lattouf, Raed, et al. "Picrosirius red staining: a useful tool to appraise collagen networks in normal and pathological tissues." Journal of Histochemistry & Cytochemistry 62.10 (2014): 751-758.
Junqueira, L. Cx U., G. Bignolas, and Ricardo R. Brentani. "Picrosirius staining plus polarization microscopy, a specific method for collagen detection in tissue sections." The Histochemical journal 11.4 (1979): 447-455.
Looss, P., et al. "A new injectable bone substitute combining poly (-caprolactone) microparticles with biphasic calcium phosphate granules." Biomaterials 22.20 (2001): 2785-94.
Gui, Liqiong, et al. "Development of novel biodegradable polymer scaffolds for vascular tissue engineering." Tissue Engineering Part A 17.9-10 (2011): 1191-1200.
Chen, D. R., J. Z. Bei, and S. G. Wang. "Polycaprolactone microparticles and their biodegradation." Polymer Degradation and Stability 67.3 (2000): 455-459.

(Continued)

*Primary Examiner* — Ali Soroush
(74) *Attorney, Agent, or Firm* — N.V. Nederlandsch Octrooibureau

(57) ABSTRACT

The present invention relates to the field of resorbing biodegradable medical and cosmetic compositions.

21 Claims, 12 Drawing Sheets

(56) References Cited

OTHER PUBLICATIONS

Bat, Erhan, et al. "In vivo behavior of trimethylene carbonate and ϵ-caprolactone-based (co) polymer networks: Degradation and tissue response." Journal of Biomedical Materials Research Part A 95.3 (2010): 940-949.
Alves, Antoine, et al. "Computerized histomorphometric study of the splenic collagen polymorphism: A control-tissue for polarization microscopy." Microscopy research and technique 78.10 (2015): 900-907.
Rich, Lillian, and Peter Whittaker. "Collagen and picrosirius red staining: a polarized light assessment of fibrillar hue and spatial distribution." Journal of morphological sciences 22.2 (2017): 0-0.

* cited by examiner

RESORBABLE BIODEGRADABLE MEDICAL AND COSMETIC COMPOSITION COMPRISING POLY(1,3-TRIMETHYLENE CARBONATE)

FIELD OF THE INVENTION

The present invention relates to the field of resorbing biodegradable medical and cosmetic compositions.

BACKGROUND ART

With increasing age and/or as a consequence of certain diseases, the body's soft tissues including muscle, skin and fat can diminish, affecting appearance and/or diminishing function. For example, sphincter muscles that control many of the body's autonomic functions such as control of bladder function and gastric reflux diminish with age and disease. Several medical and cosmetic filler compounds (also referred to as tissue augmentation compounds or tissue correction compounds) have already been developed. Fillers of animal origin, such as the injectable bovine collagen, have several drawbacks relating mainly to the risk of allergy and the threat of diseases such as Kreutzfeld Jacob's disease. As an alternative for injectable bovine collagen, other filler implants comprising a suspension or emulsion of particles made of polymeric lactic acid and/or glycolic acid repeat units (US 2003/093157 and WO 98/56431) have been developed. Other fillers are based on e.g. poly-ε-caprolactone (PCL) (WO2009/014441) or hyaluronic acid (HA) (Wang et al, 2007).

A key feature of an effective, long lasting dermal filler is that it induces a foreign body response in an extent that results in the de novo synthesis of collagen, preferably type III collagen and in addition preferably ultimately in type I collagen. In fact, but without being bound by theory, the ideal foreign body response to a long lasting dermal filler is limited to the de novo synthesis of collagen, preferably type III collagen and more preferably also and ultimately type I collagen, in addition to the resorption of the product; the collagen formation should be a result of a normal foreign body response and tissue reorganization and healing. A too strong foreign body response to the filler and/or any compound thereof may result in severe inflammation, formation of nodules and other unwanted effects.

The prior art fillers have several drawbacks. The in vivo resorption of uncrosslinked, linear HA is quite fast, as it is typically resorbed within a few days or weeks. To increase resorption time, HA requires chemical crosslinking. A chemical crosslinker can be, however, toxic, and residual crosslinker amounts are present in the injected crosslinked HA that is used for tissue augmentation. In addition, the degradation of HA results in the formation of acidic products which may induce and/or enhance the inflammatory response. Importantly, there is no evidence of that HA fillers stimulate de novo synthesis and production of significant amounts of any type of collagen which, after complete resorption of the product, will replace the volume loss providing a sustained long-lasting effect of the filler.

One study (Wang et al, 2007) has confirmed that crosslinked HA itself does not induce collagen production. Although small collagen deposits were observed surrounding the HA filler after injection in photodamaged forearm skin, this is considered to be due to the mechanical stretching of the skin fibroblasts, as result of the injection of product and not due to the HA product or any component thereof.

Dermal fillers made with synthetic polymers such as PCL, polyglycolic acid (PGA), poly(l-lactic) acid (PLLA) also have drawbacks. First of all, these polymers are essencialy degraded through bulk erosion, and like HA, their degradation results in the inevitable formation of acidic products. Furthermore, these polymers are semi-crystalline of structure, i.e. contain both amorphous and crystalline regions, and the amorphous regions of the polymers are degraded prior to the crystalline areas. As a result, the crystalline particles that (upon degradation) remain in the surrounding tissue can change the biocompatibility profile of the product—their morphology and shape can later irritate the tissue and cause inflammation. For example, it has been found for PLLA that near the original implant site stable particles of high crystallinity formed upon degradation, which seems to be related with a subcutaneous swelling in patients three years post-operatively. A fully amorphous or non-crystalline compound for tissue augmentation is therefore preferred.

Accordingly, there is an urge for an improved synthetic filler that is resorbed essentially through a mechanism of surface erosion; that does not require crosslinking through chemical toxic compounds; that is resorbed by a process that does not release acidic by-products; preferably it has a tuneable resorption time and, importantly, induces an appropriate foreign body response with de novo synthesis of collagen, preferably type III and more preferably also and ultimately type I without undesirable side effects.

SUMMARY OF THE INVENTION

The invention provides for an in vivo resorbable composition comprising a poly(1,3-trimethylene carbonate) polymer (PTMC) and a resorbable gel carrier, wherein the gel carrier is in the form of an aqueous gel and wherein the PTMC is in the form of microparticles with a diameter ranged between 1 and 200 µm.

The invention further provides for an in vivo resorbable composition comprising a poly(1,3-trimethylene carbonate) polymer (PTMC) and a resorbable gel carrier, wherein the gel carrier is preferably in the form of an aqueous gel.

The invention further provides for the use of an in vivo resorbable composition according to the invention for the preparation of a medicament for treating a skin abnormality or disfigurement, for controlling bladder function, for controlling gastric reflux, for treating erectile dysfunction and/or premature ejaculation, for treating vocal cords, and/or for treatment of joint and cartilage diseases. The invention further provides for the use of an in vivo resorbable composition according to the invention for the treatment a skin abnormality or disfigurement, for controlling bladder function, for controlling gastric reflux, for treating erectile dysfunction and/or premature ejaculation, for treating vocal cords, and/or for treatment of joint and cartilage diseases.

The invention further provides for a method of treating a skin abnormality or disfigurement, controlling bladder function, controlling gastric reflux, treating erectile dysfunction and/or premature ejaculation, treating vocal cords, and/or treating joint and cartilage diseases comprising administration of an in vivo resorbable composition according to the invention.

The invention further provides for the use of an in vivo resorbable composition according to the invention in a cosmetic or esthetic application, preferably an application for augmenting tissue, more preferably an application as a dermal implant or dermal filler.

DETAILED DESCRIPTION OF THE INVENTION

The inventors have arrived at a compound that surprisingly has all the required features; said compound is poly (1,3-trimethylene carbonate) (PTMC). When compared to HA, PTMC results in an improved stimulation and synthesis of collagen, as observed already after four weeks (see examples herein below), creating a longer lasting effect. In view of other synthetic fillers, PTMC is an amorphous, non-crystalline, compound that is degraded enzymatically during resorption.

Consequently, the resorption of PTMC involves a surface-eroding degradation behaviour by which no acidic products are formed.

PTMC and trimethylene carbonate (TMC)-based polymers have been extensively investigated for their potential use in several biomedical applications. For example, PTMC is used in the preparation of bioresorbable orthopaedic devices and other tissue reinforcement implants, abdominal anti-adhesion barriers, scaffolds for bone tissue engineering or nerve-guided regeneration, stent coating and grafts for cardiovascular applications. In these applications, PTMC is often blended with other synthetic bioresorbable polymers such as PGA and PEG or PGA alone or the TMC monomer is co-polymerized with the corresponding monomers of the bioresorbable polymers. Gui et al (2010) for example relates to the development of a biodegradable polymer scaffold for vascular tissue engineering comprised mainly of PGA, wherein PTMC and PEG were added to modulate degradation behaviour. The application in Gui et al is not an intradermal, dermal or subcutaneous application, and importantly there is no suggestion that PTMC can induce de novo synthesis of collagen, let alone already after four weeks. In addition, the copolymer in Gui et al comprises the semi-crystalline PGA polymer, which during resorption results in acid production. Mukherjee et al (2009) relates to bioabsorbable scaffold for the growth of chondrogenic cells in cartilage tissue engineering wherein PGA was used as basic polymer with PTMC added to it. This is not an intradermal, dermal or subcutaneous application, and there is no suggestion that PTMC can induce de novo synthesis of collagen, let alone already after four weeks. In addition, the copolymer in Mukherjee et al comprises the semi-crystalline PGA, which during resorption results in acid production. Bat et al (2010) relates to the investigation of the in vivo degradation PTMC, PCL and copolymer films after subcutaneous implantation. Importantly, no evidence was found of that PTMC can induce de novo synthesis of collagen, let alone already after four weeks.

Accordingly, the invention provides for an in vivo resorbable composition comprising a poly(1,3-trimethylene carbonate) polymer (PTMC) and a resorbable gel carrier, wherein the gel carrier is preferably in the form of an aqueous gel. The gel carrier according to the invention may be any suitable gel carrier known to the person skilled in the art and may be a natural or a synthetic carrier. Said composition is herein referred to as a composition according to the invention. The term resorbable and its synonym biodegradable has herein its meaning as known in the field and typically means that the composition according to the invention will be degraded in vivo, i.e. within the body of a vertebrate, preferably a mammal. Preferably, the terms biodegradability and resorbability of the composition according to the invention are construed in view of the PTMC since this typically has a longer in vivo biodegradability and resorbability time (resorbing time) over the gel carrier.

Preferably, the resorbable gel carrier comprises the viscoelastic feature of shear thinning. Accordingly, the composition according to the invention preferably comprises the viscoelastic feature of shear thinning. The rheological term shear thinning herein has its meaning as known in the field and typically means the non-Newtonian behavior of fluids whose viscosity decreases under shear strain. Shear strain is herein defined as a strain that is parallel to an element, in contrast to a normal strain which is perpendicular to an element.

Preferably, the gel carrier is a polysaccharide gel carrier and comprises or is comprised of a polysaccharide (also referred to as a viscosity enhancing agent) selected from the group consisting of a cellulose-derivative polysaccharide, a starch, a chitin, a chitosan, a hyaluronic acid, a hydrophobically-modified polysaccharide, an alginate, a carrageenan, an agar, an agarose, an intramolecular complex of a polysaccharide, an oligosaccharide, a macrocyclic polysaccharide and a mixture thereof. More preferably, the polysaccharide gel carrier comprises or is comprised of a cellulose-derivative polysaccharide, preferably selected from the group consisting of carboxymethylcellulose, sodium carboxymethylcellulose, agar methylcellulose, hydroxypropyl methylcellulose, ethylcellulose, microcrystalline cellulose, oxidized cellulose and a mixture thereof; even more preferably the resorbable polysaccharide gel carrier comprises or is comprised of sodium carboxymethylcellulose. The person skilled in the art will comprehend that other agents may be present in the gel carrier, such as but not limited to (i) a density enhancing agent that may e.g. be selected from the group consisting of sorbitol, mannitol and fructose; other suitable density agents might also be used, (ii) a tonicity wetting agent such as a polysorbate (e.g. Tween 20, 40, 60, or 80); other suitable tonicity wetting agents may also be used. A resorbable gel carrier according to the invention may include varying amounts of a density enhancing agent and/or a tonicity wetting enhancing agent.

The composition according to the invention may be stored in a container in the form of a sterile suspension. Preferably, a container is a ready for use prefilled syringe. The composition may in an embodiment be lyophilized and reconstituted extemporaneously for injectable preparations. Alternatively, a container may be a vial. Here also as for a syringe, a vial may contain the composition according to the invention ready to be used. The water used to reconstitute extemporaneously the gel in a syringe or in a vial may be distilled water, double distilled water, sterile water or PBS (Phosphate Buffered Saline). Accordingly, the invention also provides for a container, preferably a ready to use syringe, comprising the composition according to the invention. A resorbable gel carrier according to the invention may further comprise a component selected from the group consisting of a cryoprotectant and a buffering agent. A cryoprotecting agent is a chemical which inhibits or reduces the formation of damaging ice crystals in biological tissues during cooling. Suitable cryoprotecting agents include, but are not limited to sugars and carbohydrates, such as d-mannitol, lactose, sucrose, fructose, sorbitol and dextran, with d-mannitol being preferred. The concentration of a cryoprotectant in the carrier of the gel may vary depending upon the intended application and the identity of the cryoprotectant chosen. A buffering agent is a chemical compound that is or compounds that are added to a solution to allow that solution to resist changes in pH as a result of either dilution or small additions of acids or bases. Effective buffer systems employ solutions which contain large and approximately equal concentrations of a conjugate acid-base pair (or buffering agents). A buffering agent employed herein may be any such chemical compound(s) which is pharmaceutically acceptable, including but not limited to salts (conjugates acids and/or bases) of phosphates and citrates. Preferably, the resorbable polysaccharide gel carrier comprises phosphate buffered saline (PBS).

In the composition according to the invention, the PTMC may be any PTMC known to the person skilled in the art. Preferably, the PTMC is a homopolymer, a linear polymer, a branched polymer, a copolymer, a terpolymer, a blend or composite of different types of homo/co/ter-polymers, or a crosslinked polymer. A blend of polymers according to the invention comprising PTMC preferably further comprises a polymer selected from the group consisting of PCL, PGA, PLLA, PEG, PVA and PVP. Crosslinking may be performed using any method known to the person skilled in the art, such as, but not limited to, chemical crosslinking, thermal crosslinking and crosslinking by radiation; preferred is non-chemical crosslinking (e.g. crosslinking by radiation or by heat without addition of any chemical crosslinking agent) since the chemicals used for crosslinking may be toxic. Preferably, the PTMC has a number average molecular weight (Mn) of 500 to >500,000 g/mol, preferably 500 to 600,000 g/mol, more preferably 500 to 500,000 g/mol, more preferably 100,000 to 350,000 g/mol or 50,000 to 600,000 g/mol, such as 50,000, 100,000, 125,000, 150,000, 165,000, 185,000 200,000, 225,000, 250,000, 265,000, 285,000, 300,000, 325,000, 350,000, 365,000, 385,000, 400,000, 425.00, 450,000, 465,000, 485,000, 490,000, 500,000, 525,000, 550,000, 565,000, 585,000 and 600,000 g/mol. Also preferred are ranges of number average molecular weight (Mn), such as low molecular weight of between 100,000 and 200,000 g/mol, medium molecular weight of 200,000 to 300,000 g/mol, and high molecular weight of 300,000 and 600,000 g/mol. The person skilled in the art will comprehend that the number average molecular weight (Mn) of a polymer is not exact as the figures typically listed; thus, the Mn figures may be construed as 'about' the number average molecular weight (Mn), i.e. the value±10%. Accordingly, preferably, the PTMC has a number average molecular weight (Mn) of about 500 to >about 500,000 g/mol, preferably about 500 to about 600,000 g/mol, more preferably about 500 to about 500,000 g/mol, more preferably about 100,000 to about 350,000 g/mol or about 50,000 to about 600,000 g/mol, such as about 50,000, about 100,000, about 125,000, about 150,000, about 165,000, about 185,000, about 200,000, about 225,000, about 250,000, about 265,000, about 285,000, about 300,000, about 325,000, about 350,000, about 365,000, about 385,000, about 400,000, about 425,000, about 450,000, about 465,000, about 485,000, about 490,000, about 500,000, about 525,000, about 550,000, about 565,000, about 585,000, and about 600,000 g/mol. Also preferred are ranges of number average molecular weight (Mn), such as low molecular weight of between about 100,000 and about 200,000, medium molecular weight of about 200,000 to about 300,000 and high molecular weight of about 300,000 and 600,000. Preferably, the amount of PTMC in view of total synthetic polymer is at least 40%, 45%, 50%, 55%, 60%, 65%, 70%, 75%, 80%, 85%, 90%, or at least 95%. Most preferably, the amount of PTMC in view of total synthetic polymer is 100%.

In the composition according to the invention, the PTMC may be in any form known to the person skilled in the art. Preferably, the PTMC is in the form of a particle, such as nanoparticle and microparticle; preferably, in the form of microparticle (also referred to as "microsphere"). Such PTMC particle preferably comprises at least 40%, 45%, 50%, 55%, 60%, 65%, 70%, 75%, 80%, 85%, 90%, or at least 95% PTMC. Most preferably, the PTMC particle consists essentially of PTMC or consists of 100% PTMC.

Preferably, microparticles according to the invention have at least one of the following characteristics:

i) a diameter ranged between 0.1 and 500 µm, preferably between 1 and 200 µm, more preferably between 5 and 200 µm, more preferably between 20 and 200 µm, even more preferably between 20 and 150 µm, even more preferably between 30 and 90 µm, even more preferably between 25 and 75 µm, even more preferably between 38 and 75 µm, even more preferably between 25 and 50 µm. A more preferred diameter range is 40 µm±10% or ±20%, such as a diameter ranged between 32 and 48 µm.

ii) homogenous density, form and content, preferably throughout the microparticle, iii) spherical shape (essentially round) and surface smoothness, and, iv) essentially spherical microspheres.

Preferably, such microparticles have homogenous content and density throughout the microparticle, are essentially round and have smooth surfaces.

In an embodiment, which can be combined with other embodiments, the invention provides for an in vivo resorbable composition comprising a poly(1,3-trimethylene carbonate) polymer (PTMC) and a resorbable gel carrier, wherein the gel carrier is in the form of an aqueous polysaccharide gel, wherein the PTMC is in the form of microparticles with a diameter ranged between 1 and 200 µm, and wherein the microparticles have homogenous content and density throughout the microparticle, are essentially round and have smooth surfaces. Such microparticles may have a diameter ranged between 5 and 200 µm, more preferably between 20 and 200 µm, more preferably between 20 and 150 µm, even more preferably between 25 and 150 µm, even more preferably between 30 and 90 µm, even more preferably between 25 and 75 µm, even more preferably between 38 and 75 µm, even more preferably between 25 and 50 µm. A more preferred diameter range is 40 µm±10% or ±20%, such as a diameter ranged between 32 and 48 µm.

Morphology of microparticles may be assessed using methods known in the art, e.g. using light microscopy or using scanning electron microscopy (looss et al, 2001, which is herein incorporated by reference).

In an embodiment, which can be combined with other embodiments, the invention provides for an in vivo resorbable composition comprising a poly(1,3-trimethylene carbonate) polymer (PTMC) and a resorbable gel carrier, wherein the gel carrier is in the form of an aqueous polysaccharide gel and the PTMC is in the form of a liquid polymer.

Microparticles can be produced using methods known in the art, such as e.g. the methods disclosed in looss et al (2001) and Chen et al (2000). The PTMC may be dissolved in an organic solvent such as dichloromethane (DCM). After forming of the microparticles, such as by a method in looss et al, by mixing the PTMC in an organic solvent with an aqueous liquid comprising a surfactant, the organic solvent can be removed by extraction evaporation. PTMC and/or microparticles according to the invention may be crosslinked during or after production using methods known to the person skilled in the art, as described here above.

The composition according to the invention may comprise varying amounts of PTMC, preferably microparticles, depending upon the intended application. In the composition according to the invention, the PTMC (microparticles) is/are preferably present in a concentration of about 1 to about 40 volume percent (v/v). Even more preferably, PTMC (microparticles) is/are present in a concentration of about 10 to about 30 volume percent (v/v) or 10 to 30 volume percent (v/v). Even more preferably, PTMC (microparticles) is/are present in a concentration of about 10 to about 40 volume percent (v/v), about 20 to about 40 volume percent (v/v), or about 30 to about 40 volume percent (v/v). Even more preferably, PTMC (microparticles) is/are present in a concentration of about 30 volume percent (v/v).

In the composition according to the invention, the PTMC (microparticles) is/are preferably present in a concentration of 1 to 40 volume percent (v/v). Even more preferably, PTMC (microparticles) is/are present in a concentration of 10 to 30 volume percent (v/v) or 10 to 30 volume percent (v/v). Even more preferably, PTMC (microparticles) is/are present in a concentration of 10 to 40 volume percent (v/v), 20 to 40 volume percent (v/v), or 30 to 40 volume percent (v/v). Even more preferably, PTMC (microparticles) is/are present in a concentration of 30 volume percent (v/v).

In the composition according to the invention, the gel carrier material is present in a concentration of about 0.2 to about 20 weight percent (w/w). More preferably, the gel carrier material is present in a concentration of 0.2 to 20 weight percent. Even more preferably, the gel carrier material is present in a concentration of about 1 to about 5 weight percent; even more preferably, the gel carrier material is present in a concentration of 1 to 5 weight percent. Preferably, at least about 0.2, 0.3, 0.4, 0.5, 0.6, 0.7, 0.8, 0.9, 1.0, 1.2, 1.4, 1.6, 1.8, 2.0, 2.2, 2.4, 2.6, 2.8, 3.0, 3.1, 3.2, 3.3, 3.4, 3.5, 3.6, 3.7, 3.8, 3.9, 4.0, 4.1, 4.2, 4.3, 4.4, 4.5, 4.6, 4.7, 4.8, 4.9, or 5 weight percent of the gel carrier material is present and at most about 20, 19, 18, 17, 16, 15, 14, 13, 12, 11, 10, 9, 8, 7, 6, 5, 4.9, 4.8, 4.7, 4.6, 4.5, 4.4, 4.3, 4.2, 4.1, 4.0, 3.9, 3.8, 3.7, 3.6, 3.5, 3.4, 3.3, 3.2, 3.1, 3.0, 2.8, 2.6, 2.4, 2.2, 2.0, 1.8, 1.6, 1.4, 1.2, 1.0, 0.9, 0.8, 0.7, 0.6, 0.5, 0.4, or 0.3 weight percent is present. More preferably, at least 0.2, 0.3, 0.4, 0.5, 0.6, 0.7, 0.8, 0.9, 1.0, 1.2, 1.4, 1.6, 1.8, 2.0, 2.2, 2.4, 2.6, 2.8, 3.0, 3.1, 3.2, 3.3, 3.4, 3.5, 3.6, 3.7, 3.8, 3.9, 4.0, 4.1, 4.2, 4.3, 4.4, 4.5, 4.6, 4.7, 4.8, 4.9 or 5 weight percent of the gel carrier material is present and at most 20, 19, 18, 17, 16, 15, 14, 13, 12, 11, 10, 9, 8, 7, 6, 5, 4.8, 4.6, 4.4, 4.2, 4.0, 3.8, 3.6, 3.4, 3.2, 3.0, 2.8, 2.6, 2.4, 2.2, 2.0, 1.8, 1.6, 1.4, 1.2, 1.0, 0.9, 0.8, 0.7, 0.6, 0.5, 0.4, or 0.3 weight percent is present. A preferred range of gel carrier material is from about 0.2 to about 8 weight percent, a more preferred range is from about 0.4 to about 7 weight percent, a more preferred range is from about 0.5 to about 6 weight percent, a more preferred range is from about 0.6 to about 5 weight percent, a more preferred range is from about 1 to about 5 weight percent. A preferred range of resorbable polysaccharide of the gel carrier is from 0.2 to 8 weight percent, a more preferred range is from 0.4 to 7 weight percent, a more preferred range is from 0.5 to 6 weight percent, a more preferred range is from 0.6 to 5 weight percent, a more preferred range is from 1 to 5 weight percent. A preferred range of gel carrier is from 0.8 to 5 weight percent, a more preferred range is from 1 to 4 weight percent, a more preferred range is from 1.8 to 4 weight percent, a more preferred range is from 2 to 4 weight percent, a more preferred range is from 3 to 4 weight percent, a more preferred range is from 3.5 to 4 weight percent. Preferably, the composition according to the invention has a viscosity of about 5,000 to about 5,000,000 mPa·s at room temperature. Viscosity is preferably measured under atmospheric conditions and at room temperature, which is 20 degrees Celsius, and measurement is preferably performed with a rotational viscometer (e.g. Brookfield Viscometer DV2T) equipped with a suitable spindle (e.g. LV or T-Bar series) to generate a suitable torque (typically 50-75%) when a rotational speed of 1 RPM is applied.

In the composition according to the invention, a further compound may be present, preferably an active compound, preferably an anesthetic. Exemplary anesthetics include, but are not limited to, lidocaine, novocaine, benzocaine, prilocaine, ripivacaine, and propofol. Other medicaments that can be employed in a composition according to the invention include: a peptide, a tissue regeneration agent, an antibiotic, a steroid, fibronectin, a cytokine, a growth factor, an analgesic, an antiseptic, alpha-, beta, or gamma-interferon, erythropoietin, a glucagon, calcitonin, heparin, interleukin-1, interleukin-2, filgrastim, cDNA, DNA, RNA, a protein, a peptide, Human Growth Hormone (HGH), luteinizing hormone, atrial natriuretic factor, Factor VIII, Factor IX, RNA, an antibody, a chemotherapeutic, follicle-stimulating hormone and combinations thereof. The further compound may also be an excipient, such excipient is preferably of pharmaceutical grade. A preferred excipient is glycerol. Glycerol will render the composition more lubricious. Preferably, glycerol is present in a concentration of about 0.05 to about 5 weight percent (w/w). More preferably, glycerol is present in a concentration of about 0.1 to about 4 weight percent, more preferably in a concentration of about 0.2 to about 2 weight percent. Preferably, glycerol is present in a concentration of 0.05 to 5 weight percent (w/w). More preferably, glycerol is present in a concentration of 0.1 to 4 weight percent, more preferably in a concentration of 0.2 to 2 weight percent.

Preferably, all compounds of the composition according to the invention are biocompatible. Preferably, the composition according to the invention, which comprises a resorbable gel carrier (preferably an aqueous gel) and is an aqueous composition, is buffered to keep the composition at physiological pH, i.e. about pH 7.4. The person skilled in the art knows how to buffer a solution and will select the proper buffering compound. The buffering compound may be, but is not limited to, a phosphate and/or citrate.

Preferably, the composition according to the invention is a pharmaceutical composition, meaning that all compounds and the entire combination (i.e. the composition) is of pharmaceutical grade.

Alternatively, or in combination with the previous, the composition according to the invention is a cosmetic or esthetic composition. This does not exclude the composition being of pharmaceutical grade but means that it is (also) suitable for cosmetic or esthetical use.

Preferably, the composition according to the invention is suitable for augmenting tissue, preferably soft tissue such as connective tissue like tendons, ligaments, fascia, skin, fibrous tissues, fat, and synovial membranes, preferably an implant or filler for intradermal, deep-dermal, subdermal or subcutaneous use.

The invention further provides for the medical use of the composition according to the invention. Accordingly, the invention provides for a composition according to the invention for use as a medicament, preferably for treating a skin abnormality or disfigurement, for controlling bladder function (treatment of urinary sphincter deficiency), for controlling gastric reflux (treatment of pyloric sphincter deficiency), for treating erectile dysfunction and/or premature ejaculation, for treating congenital abnormalities, for filling up gums for dental treatment, for treating vocal cords, and/or for joint and cartilage lubrication (treatment of osteoarthritis). The invention further provides for the use of a composition according to the invention for the preparation of a medicament for treating a skin abnormality or disfigurement, for controlling bladder function (treatment of urinary sphincter deficiency), for controlling gastric reflux (treatment of pyloric sphincter deficiency), for treating erectile dysfunction and/or premature ejaculation, for treating congenital abnormalities, for filling up gums for dental treatment, for treating vocal cords, and/or for joint and cartilage lubrication (treatment of osteoarthritis). The invention further provides for the use of a composition according to the invention for the treatment of a skin abnormality or disfigurement, for controlling bladder function (treatment of urinary sphincter deficiency), for controlling gastric reflux (treatment of pyloric sphincter deficiency), for treating erectile dysfunction and/or erectile dysfunction, for treating congenital abnormalities, for filling up gums for dental treatment, for treating vocal cords, and/or for joint and cartilage lubrication (treatment of osteoarthritis). The invention further provides for a method of treating a skin abnormality or disfigurement, for controlling bladder function (treatment of urinary sphincter deficiency), for controlling gastric reflux (treatment of pyloric sphincter deficiency), for treating erectile dysfunction and/or premature ejaculation, for treating congenital abnormalities, for filling up gums for dental treatment, for treating vocal cords, and/or for joint and cartilage lubrication (treatment of osteoarthritis) comprising administration of a composition according to the invention to a subject, preferably a mammal, preferably a human. Further medical use of the composition according to the invention is cartilage replacement, reinforcement, lubrication, and/or regeneration.

In an embodiment, a composition according to the invention is used as an implant or filler to treat various sphincter deficiencies such as urinary incontinence (control of bladder function). Loss of bladder control may be due to stress due to physical movement (coughing, sneezing, exercising) and/or to urge or leakage of large amounts at unexpected times, including sleep. All types of incontinences may be treated using a composition according to the invention regardless of the patient's age. Continence is dependent upon a compliant reservoir and sphincter efficiency that has two components: (i) the involuntary smooth muscle on the bladder neck; and (ii) the voluntary skeletal muscle of the external sphincter. Therefore, a composition according to the invention may be added to localize compression to the sphincter muscle or urethra, thereby reducing the lumen size through one or more injections of the composition according to the invention and thus substantially reduce or eliminate urinary stress incontinence. In these instances, a composition according to the invention may be inserted by injection into urethral or periurethral tissue. Thus, a typical procedure involves injecting a composition according to the invention with the aid of a cystoscope into the tissues around the neck of the bladder creating increased tissue bulk, and subsequent coaptation of the urethral lumen. A composition according to the invention adds bulk and helps to close the urethra to reduce stress incontinence. The injection may typically be repeated periodically for optimal results.

In an embodiment, a composition according to the invention is used as a filler or as an implant for controlling gastric reflux (to treat a deficiency of the pyloric sphincter). Gastroesophageal reflux disease (GERD) involves the regurgitation of stomach gastric acid and other contents into the oesophagus or diaphragm. 70% of reflux episodes occur during spontaneous relaxations of the lower oesophageal sphincter, or due to a prolonged relaxation after swallowing. 30% occur during periods of low sphincter pressure. The primary symptom is heart burn (30 to 60 minutes after meals). Atypical manifestations of GERD include: asthma; chronic cough; laryngitis; sore throat; and non-cardiac related chest pain. GERD is a lifelong disease that requires lifestyle modifications as well as medical intervention. Therefore, a composition according to the invention may be injected to add bulk and localize compression to the lower oesophageal sphincter. Thus, a typical procedure involves injecting a composition according to the invention with the aid of an endoscope into the tissues around the lower oesophageal sphincter creating increased tissue bulk, and subsequent coaptation, normalizing sphincter pressure. A composition according to the invention adds bulk and helps to close the sphincter to reduce reflux. The injection may be repeated yearly for optimal results. A composition according to the invention may be injected using local anesthesia.

In an embodiment, a composition according to the invention is used as a filler or as an implant for treating erectile dysfunction (ED) that may affect men of all ages. A composition according to the invention may be used for treating ED. A typical procedure involves injecting a composition according to the invention directly at the deep fascia throughout the length of the corpus cavernosum.

In an embodiment, a composition according to the invention is used as a filler or as an implant for treating vocal cords. A composition according to the invention may be used for intra-cordal injections of the laryngeal voice generator by changing the shape of this soft tissue mass. The invention further provides for the use of a composition according to the invention in a cosmetic application, preferably an application for augmenting tissue, more preferably an application as a dermal implant or dermal filler.

In this document and in its claims, the verb "to comprise" and its conjugations is used in its non-limiting sense to mean that items following the word are included, but items not specifically mentioned are not excluded. In addition, reference to an element by the indefinite article "a" or "an" does not exclude the possibility that more than one of the element is present, unless the context clearly requires that there be one and only one of the elements. The indefinite article "a" or "an" thus usually means "at least one".

The word "about" or "approximately" when used in association with a numerical value (e.g. about 10) preferably means that the value may be the given value (of 10) more or less 10% of the value. All patent and literature references cited in the present specification are hereby incorporated by reference in their entirety.

The present invention has been described above with reference to a number of exemplary embodiments. Modifications and alternative implementations of some parts or elements are possible, and are included in the scope of protection as defined in the claims.

The present invention is further described by the following examples which should not be construed as limiting the scope of the invention.

REFERENCES

Wang et al (2007); Arch Dermatol Vol 143, 155-163; In Vivo Stimulation of De Novo Collagen Production Caused by Cross-linked Hyaluronic Acid Dermal Filler Injections in Photodamaged Human Skin.

Gui et al (2010); Tissue Engineering: Part A, Volume 17, Numbers 9 and 10, 1191-1200; Development of Novel Biodegradable Polymer Scaffolds for Vascular Tissue Engineering.

Mukherjee et al (2010); Journal of Biomedical Materials Research Part B: Applied Biomaterials, 92-102 Effect of 3D-Microstructure of Bioabsorbable PGA:TMC Scaffolds on the Growth of Chondrogenic Cells.

Bat et al (2010); Journal of Biomedical Materials Research A|1 Dec. 2010 VOL 95A, ISSUE 3, 940-949.

looss et al (2001); Biomaterials 22, 2785-2794; A new injectable bone substitute combining polyts-caprolactone) microparticles with biphasic calcium phosphate granules.

Chen et al (2000); Polymer degradation and Stability 67, 455-459; Polycaprolactone Microparticles and their Biodegradation.

Suvarna K S et al (2018); Bancroft's Theory and Practice of Histological Techniques, 8th ed by Kim S Suvarna, Christopher Layton and John D. Bancroft.

Junqueira L C at al (1979); Histochem J 1979, 11(4):447-55; Picrosirius staining plus polarization microscopy, a specific method for collagen detection in tissue sections.

Alves A et al (2015); Microsc Res Tech 2015, 78(10):900-7; Computerized histomorphometric study of the splenic collagen polymorphism: A control-tissue for polarization microscopy.

Lattouf R et al (2014); J Histochem Cytochem 2014, 62(10): 751-758; Picrosirius Red Staining: A Useful Tool to Appraise Collagen Networks in Normal and Pathological Tissues.

Whittaker P et al (2005); Braz J Morphol Sci 2005, 22(2): 97-104; Collagen and Picrosirius Red Staining: A Polarized Light Assessment of Fibrillar Hue and Spatial Distribution.

EXAMPLES

Figure 1:
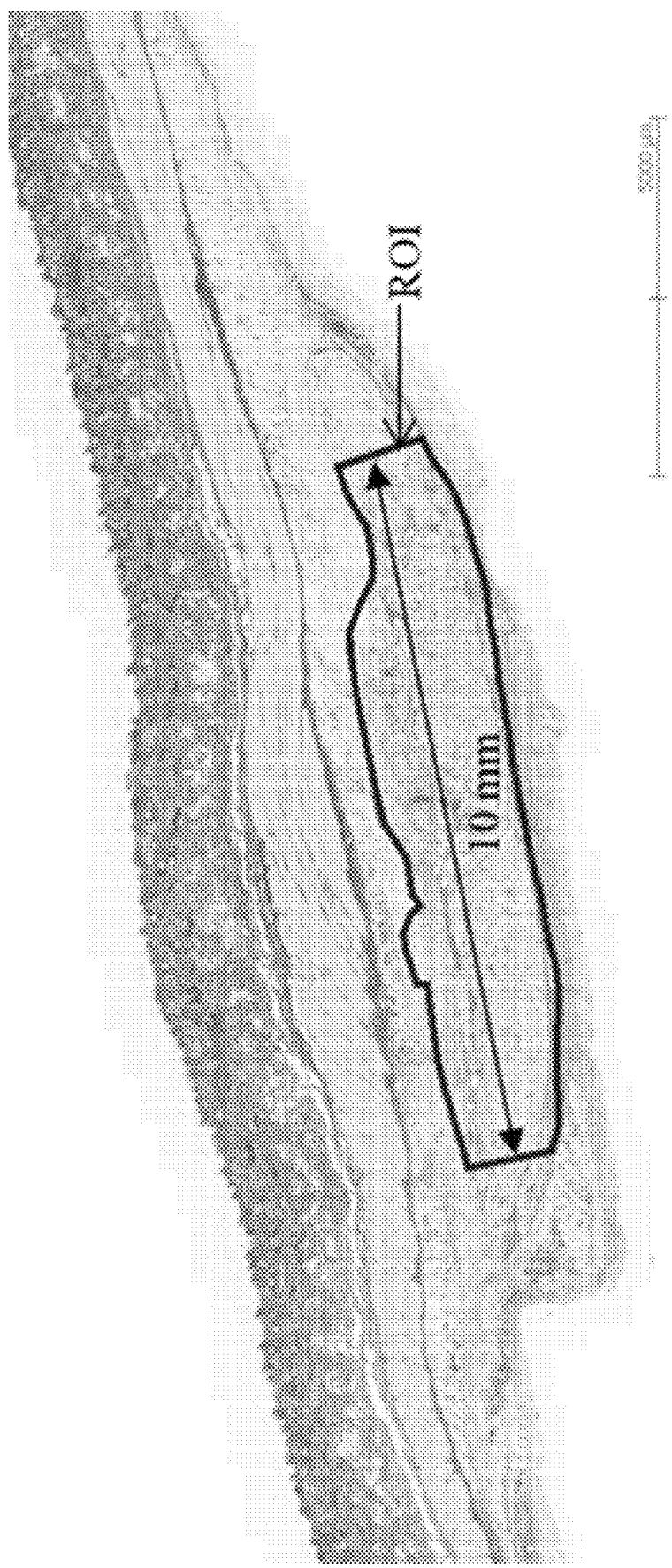
FIG. 1 depicts the histomorphometric evaluation of collagen; a representative photomicrograph of the location of the standardized region of interest is given (Picrosirius red stained section).

Example 1 Stimulation of Production of Natural De Novo Collagen by a Composition According to the Invention Objective:

The objective of this study is to assess the potential of a dermal filler comprising representative PTMC microspheres according to the invention to stimulate natural de novo collagen production after injection in an animal model.

Main Outcome Measure:

Histology analysis of de novo synthesis of collagen, for example type I and type III collagen.

Materials:

A dermal filler according to the invention (test product), a commercially available HA dermal filler, a gel carrier according to the invention (control 1) and saline solution (control 2).

Animals:

Study is carried out in a total of three rabbits (New Zealand White). Test, comparator and control materials are injected into the same animal.

Injection Sites:

Subdermal injections are investigated. Injections are performed on both sides of the spinal column of the animal model. Test, comparator and control materials are injected into the same animal; two injections per material (one on each side), 10 injections per animal. Injections are performed to create a bolus of 0.2 mL.

Evaluation Time-Points:

Evaluations are carried out at week 4, week 12, and week 36 after injection, at which one rabbit per time-point is euthanized by intravenous injection of sodium pentobarbital. Each of the injection areas are explanted and immediately processed for histological analysis.

Histological Staining and Analysis:

Histological sections are stained with the routine haematoxylin and eosin dyes (1). Trichrome (2) and/or Picro-Sirius red staining (3) are performed for specific collagen detection.

Results:

The dermal filler according to the invention stimulates natural collagen production significantly better than the comparator product and control.

(1): Most widely used and important general purpose stain combination. May be used after any fixation except fixation with osmium tetroxide. Hematoxylin, a natural dye product, acts as a basic dye that stains blue or black. Nuclear heterochromatin stains blue and the cytoplasm of cells rich in ribonucleoprotein also stains blue. The cytoplasm of cells with minimal amounts of ribonucleoprotein tends to be lavender in colour. The aniline dye, eosin, is an acid dye that stains cytoplasm, muscle, and connective tissues various shades of pink and orange.

(2): The Trichrome Stain (Connective Tissue Stain) is intended for use in the histological visualization of collagenous connective tissue fibers in tissue sections.

(3): The Picro-Sirius Red Stain is intended for use in the histological visualization of collagen I and III fibers in addition to muscle in tissue sections. The PSR stain may be viewed using standard light microscopy or polarized light resulting in birefringence of the collagen fibers to distinguish between type I and type III.

Example 2 Stimulation of Production of Natural De Novo Collagen by Three Compositions According to the Invention Objective The objective of this study was to demonstrate the potential of a dermal filler according to the invention comprising poly(trimethylene carbonate) (PTMC) microspheres to stimulate natural de novo collagen production when compared to commercially available hyaluronic acid (HA)-based products, following subcutaneous administration of the compositions by injection in rabbits.

Materials and Methods

Dermal fillers Test articles 1-3 were prepared by mixing PTMC microspheres with an aqueous gel-carrier made of carboxymethyl cellulose (CMC) at a concentration of 3.9% in phosphate-buffered saline pH 7.4, to obtain a clear gel with a minimum viscosity of 50,000 mPa·s. PTMC microspheres were prepared by a solvent extraction method such as described in Iooss et al (2001). Typically, PTMC polymers with of number average molecular weight of 100,000 g/mol (Test article 1), 250,000 g/mol (Test article 2) and 490,000 g/mol (Test article 3) were dissolved in dichloromethane at concentrations of 5.0%, 3.5% and 1.9%, respectively. A total of 100 mL of the polymer solution was then emulsified in 1L of water containing 3% (w/w) of poly(vinyl alcohol) under continuous mechanical stirring at 750 rpm. After extraction of the solvent, the formed microspheres were filtrated to collect particles with a diameter ranging between 20 and 200 μm for gamma irradiation at 100 kGy. After irradiation, the PTMC microspheres were washed, mixed into the gel-carrier at a concentration of 30% (v/v), and the resultant product filled into syringes. Test article 4 was consisted of the gel-carrier only, i.e. without the PTMC microspheres.

Two commercially available HA-based dermal fillers were used in this study: HA Comparator 1, Juvéderm® Ultra 3 (Allergan Laboratories, USA), and HA Comparator 2, Restylane® Defyne (Galderma Laboratories, USA). Juvéderm® ULTRA 3 is a crosslinked non-animal HA gel at a concentration of 24 mg/mL in phosphate buffer pH 7.2, and 3 mg/mL of lidocaine hydrochloride. Restylane® Defyne contains non-animal crosslinked sodium hyaluronate at concentration of 20 mg/mL in phosphate buffered saline at pH 7, and 3 mg/mL lidocaine hydrochloride.

Study Design

Two rabbits, one per time point, each received ten subcutaneous injections of 200 μl of the test or comparator articles, two sites per test article and one site per comparator product. After 4 and 12 weeks of implantation, quantitative evaluation of the total collagen content (TCC) and the collagen remodelling index (CRI) was performed through histomorphometric analysis. A qualitative and semi-quantitative histopathological analysis of local tissues effects including inflammatory response at the injection sites was also reported. This study was conducted in adaptation to the ISO 10993-6, Biological Evaluation of Medical Devices, Part 6 (2016): Tests for Local Effects after Implantation. At the end of each observation period, the assigned rabbit was anesthetized and one subcutaneous injections of 200 μL of each article was administrated in the back skin of the animal to obtain a baseline for histologic characterization and analysis of degradation (T0 sites). Animals were sacrificed by an injectable barbiturate, and the implanted sites were excised (specimens of approximately 2×2 cm, encompassing the skin and intradermal layer), formalin-fixated and embedded in paraffin and processed for histology. For all articles and corresponding T0, four central sections were cut with a microtome (4-7 μm thickness) and stained with a modified Masson's trichrome, safranin-hematoxylin-eosin (SHE), Alcian blue and picrosirius red, respectively. SHE and Alcian blue provided cellular organization and extracellular matrix structure information. Trichrome and picrosirius red stains highlight collagen content with blue and red coloured stains, respectively (Suvarna K S et al, 2018). Picrosirius red-stained slides were further analysed under polarized light to ascertain collagen remodelling. Under polarized light, collagen maturity and fiber thickness are indicated by differences in colour: immature/thin fibers appear green/yellow and mature/thick fibers appear orange/red (Junqueira L C et al, 1979, Alves A et al, 2015).

For the histomorphometric analysis, a standardized region of interest (ROI) was manually defined in the center of the injected site (over approximately 10 mm) to encompass the implanted material (representative picture in FIG. 1). All sections were examined using a digital slide scanner microscope (AxioScan.Z1, ZEISS, France) and the image analyzer system CALOPIX version 3.2.0 (TRIBVN, France).

Results

Histomorphometric Analysis—Collagen Evaluation

The healing phase secondary to prosthetic implantation or wound creation is associated with collagen remodelling: thin immature (type III) collagen fibers deposited during the early phase are progressively replaced by thick mature (type I) collagen fibers.

Collagen is specifically coloured by the picrosirius red stain which allows the quantification of the total collagen content. Moreover, following picrosirius red staining and using cross-polarization microscopy, collagen fibers are highly birefringent and display variable shade based on the amount of type I and III collagen, the fiber thickness and packing, and the collagen molecular organization (Junqueira L C et al, 1979). Thin, loosely-arranged, immature fibers appear green while thicker, densely-packed, mature fibers appear red-orange (Alves A et al, 2015). The ratio of green to red-orange fibers at the level of the healing tissue can be quantified and is considered to be indicative of the collagen matrix remodelling process (Lattouf R et al, 2014). A picrosirius red-stained section of a lymphoid organ (rat spleen) prepared under the same conditions was used as a positive control to define the angle of polarization based on the collagen network of the splenic capsule and trabeculae, as described elsewhere (Whittaker P et al, 2005).

Total Collagen Content (TCC)

Figure 2:
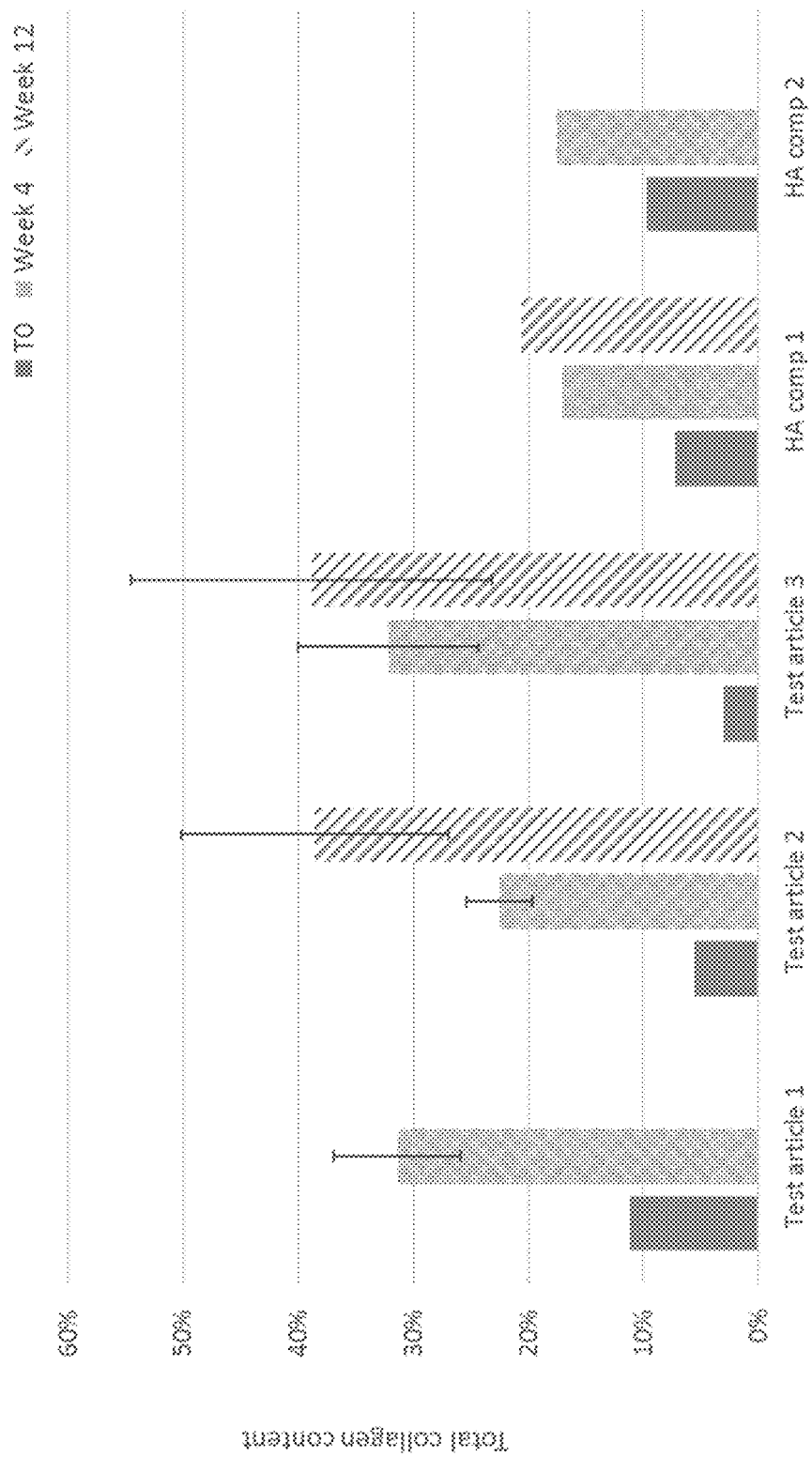
FIG. 2 depicts the percentage of total collagen content within the implanted area after 4 and 12 weeks of subcutaneous implantation in rabbits. Quantification at 12 weeks was not performed for Test article 1 and HA comparator 2 due to technical reasons.
Figure 3A:
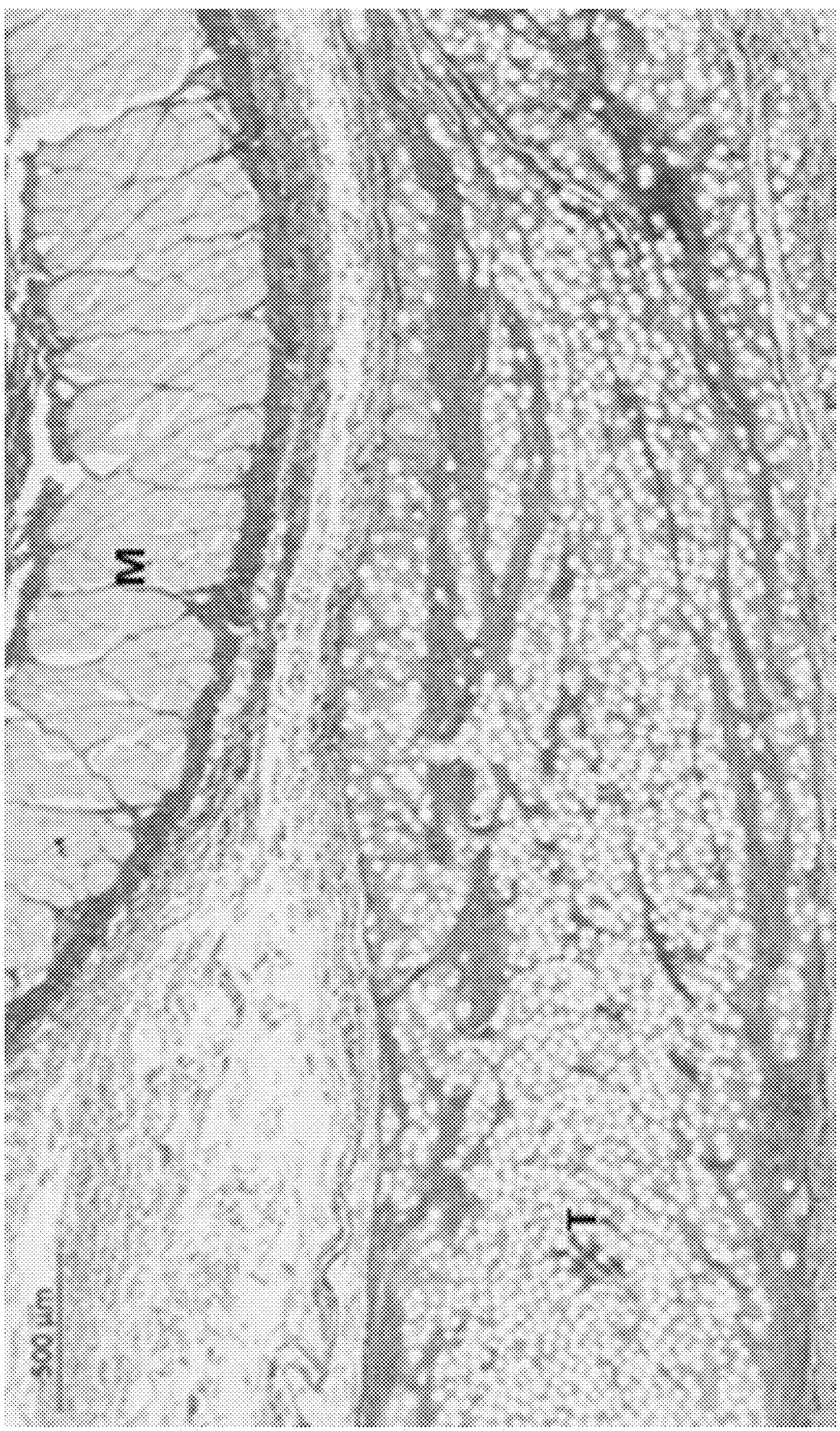
FIG. 3 depicts representative photomicrographs of Test article after 4 weeks (A) and 12 weeks (B) of subcutaneous implantation in rabbits and HA-based comparator product after 4 weeks (C) and 12 weeks (D) of subcutaneous implantation in rabbits. Picrosirius red was used for the staining of the histological sections. M: cutaneous muscle; T: Test article; HA: HA based comparator.
Figure 3B:
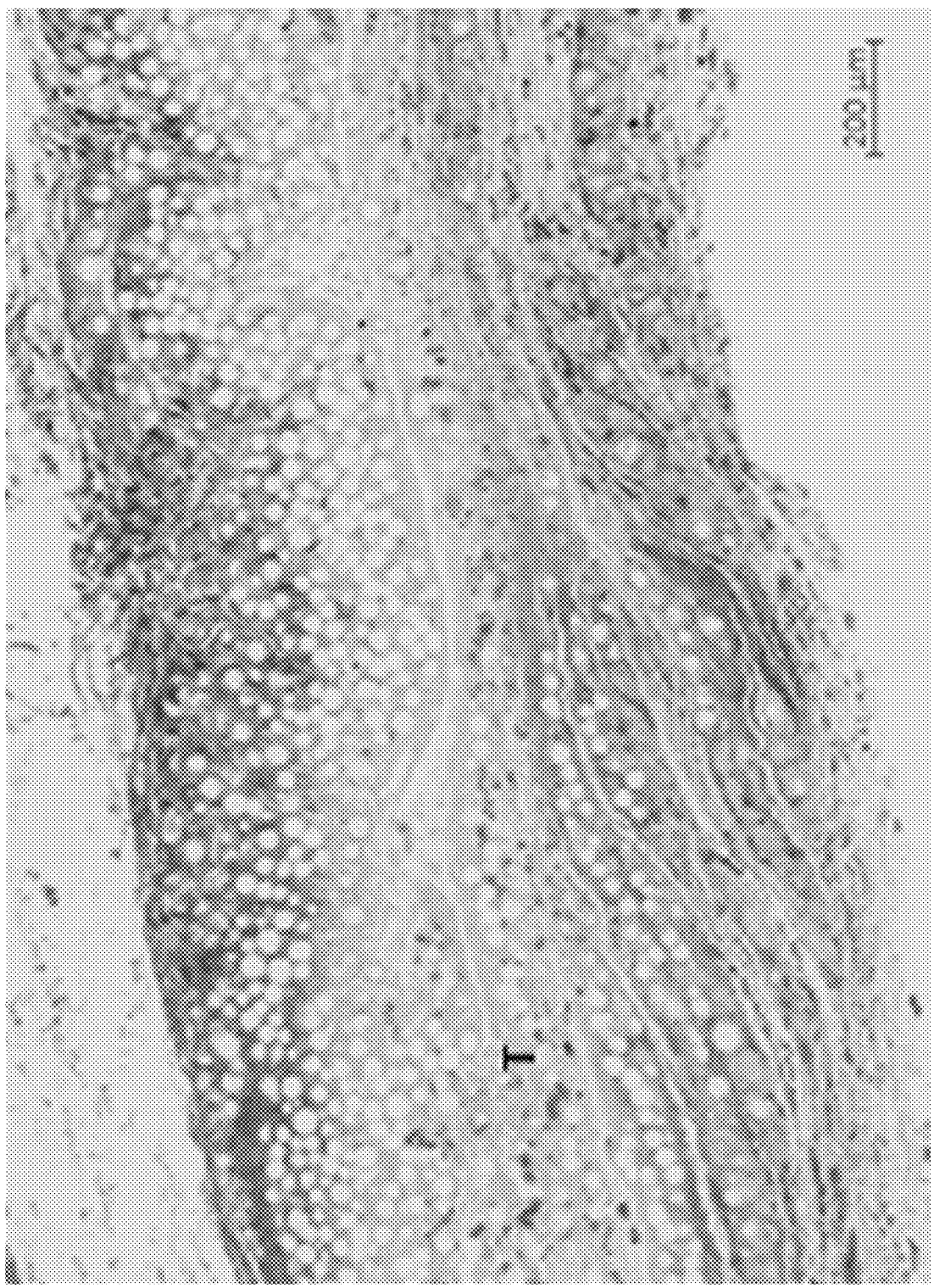
Figure 3C:
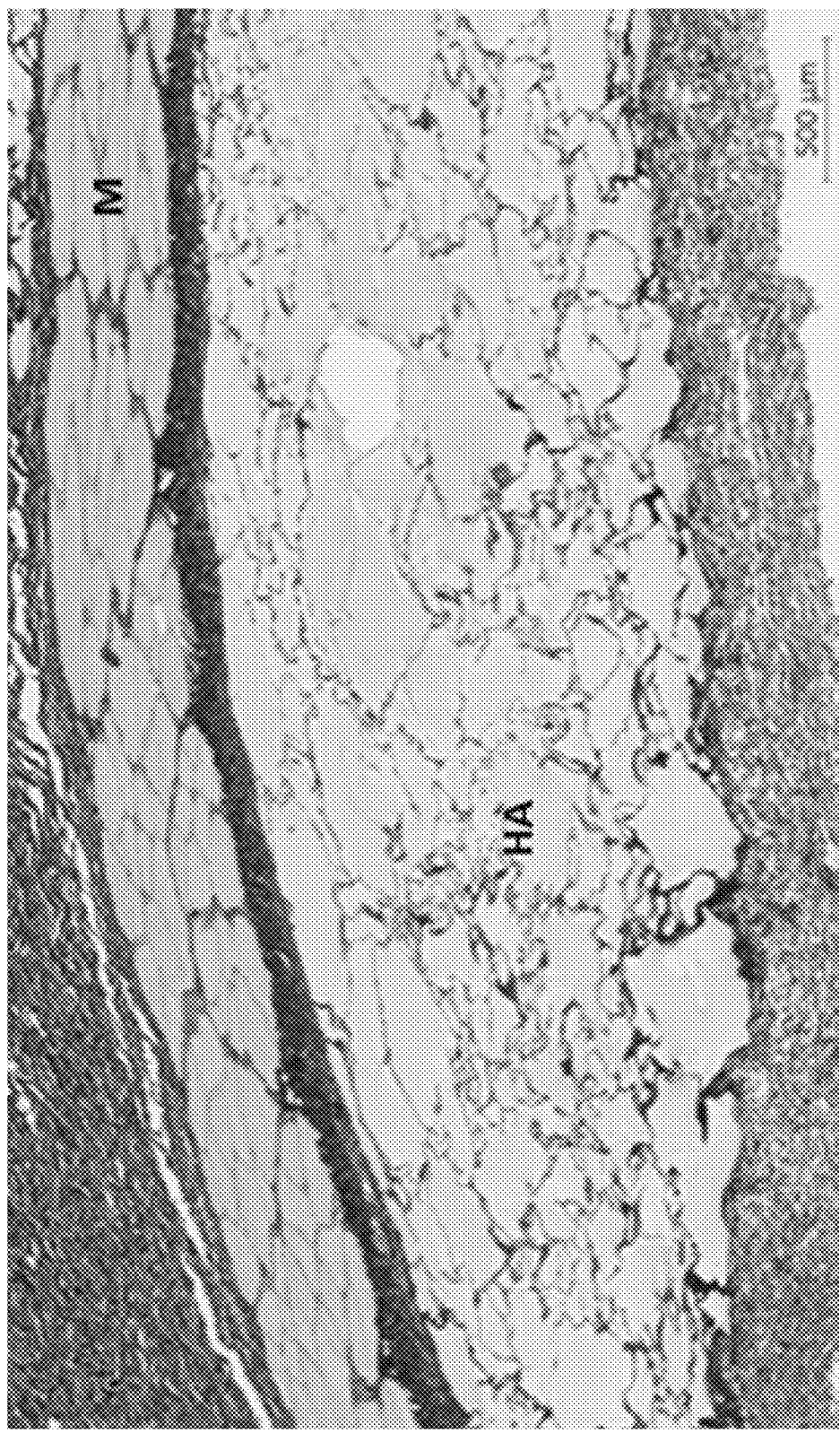
Figure 3D:
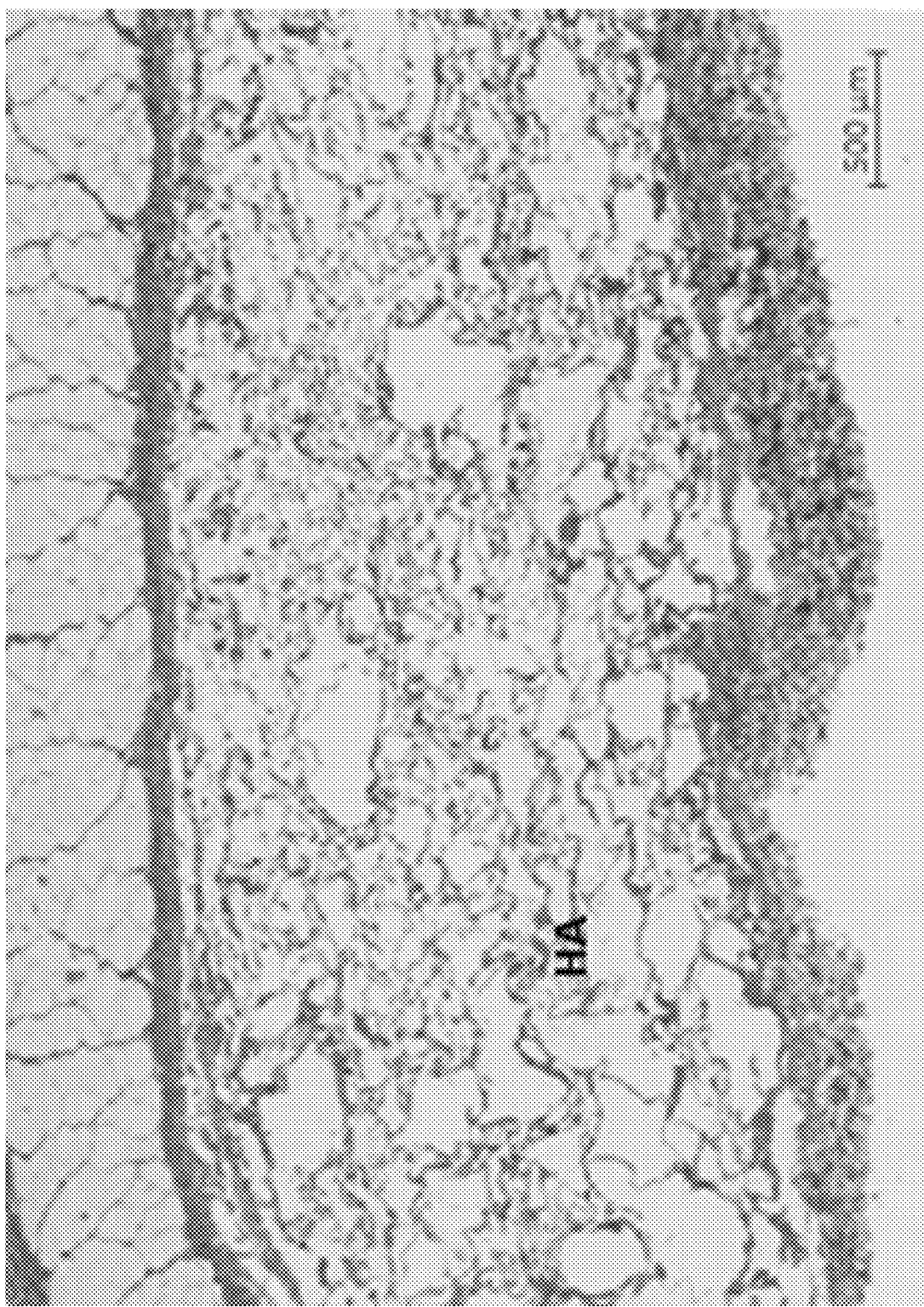

Digitized picrosirius red-stained sections were examined with a bright-field microscope to calculate the TCC at 4 and 12 weeks of implantation. Results were expressed as the percentage of collagen surface area measured within the selected ROI and are summarized in FIG. 2. Representative photomicrographs of the histological stained sections used in this evaluation are shown in FIG. 3.

Figure 6:
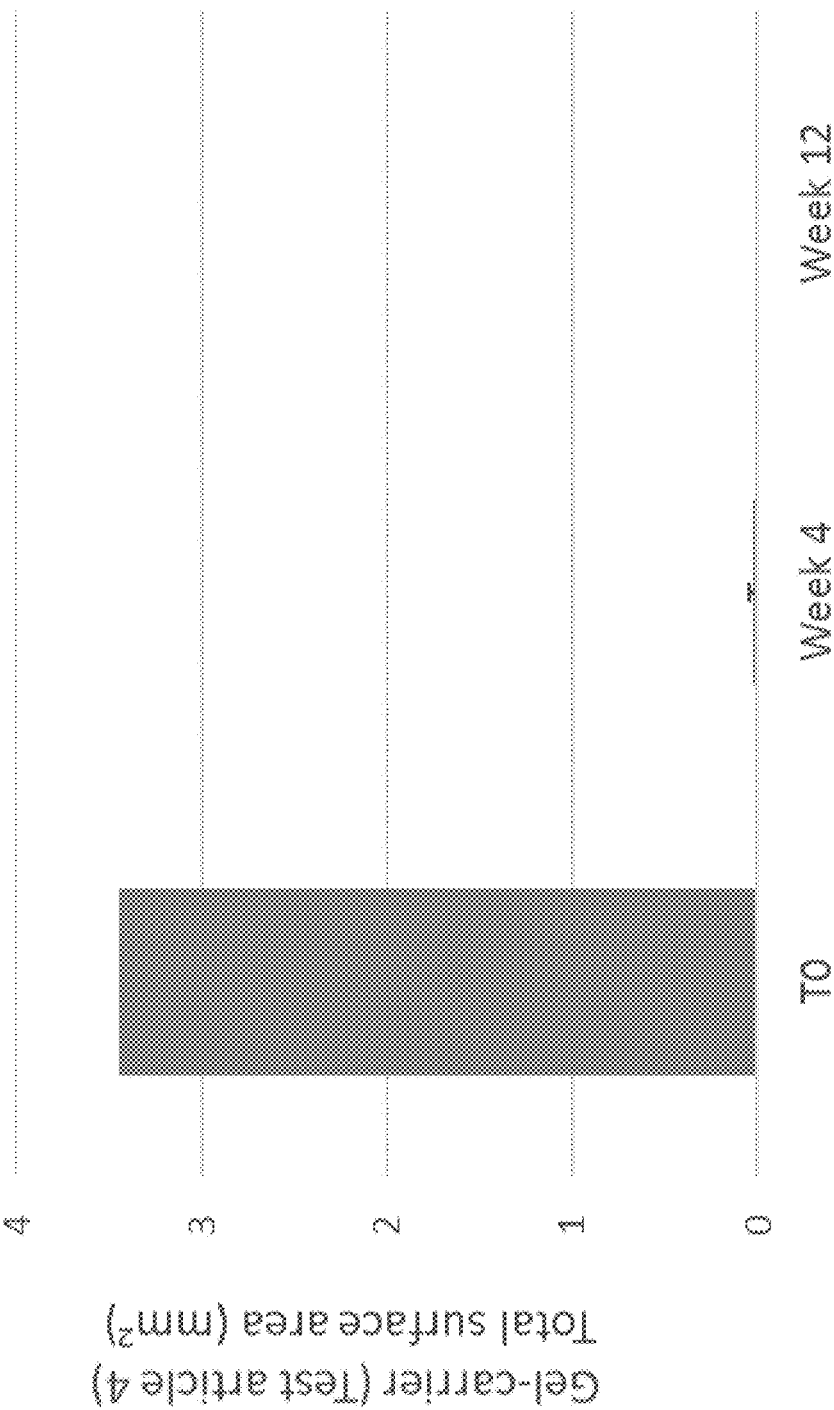
FIG. 6 depicts degradation of the Test article 4 (gel-carrier only)—The total surface area after 4 and 12 weeks of subcutaneous implantation in rabbits was determined.

After 4 weeks of implantation, the percentage of collagen determined within the implant sites was already increased by approximately two-fold for test articles 1 to 3 when compared to the HA-based dermal fillers. Test article 4, the gel-carrier only, was completely degraded after 4 weeks of implantation, and the collagen content was not quantified (FIG. 6). These results indicate that the stimulation to produce native collagen is, in fact, due to the presence of the PTMC microspheres. After 12 weeks, the percentage of total collagen remained greater in the test articles 2 to 3 compared to of the HA-based dermal fillers implanted. Total collagen content for product 1 and HA comparator 2 was not determined due to technical reasons during histological preparation.

Collagen Remodelling Index (CRI)

Figure 4:
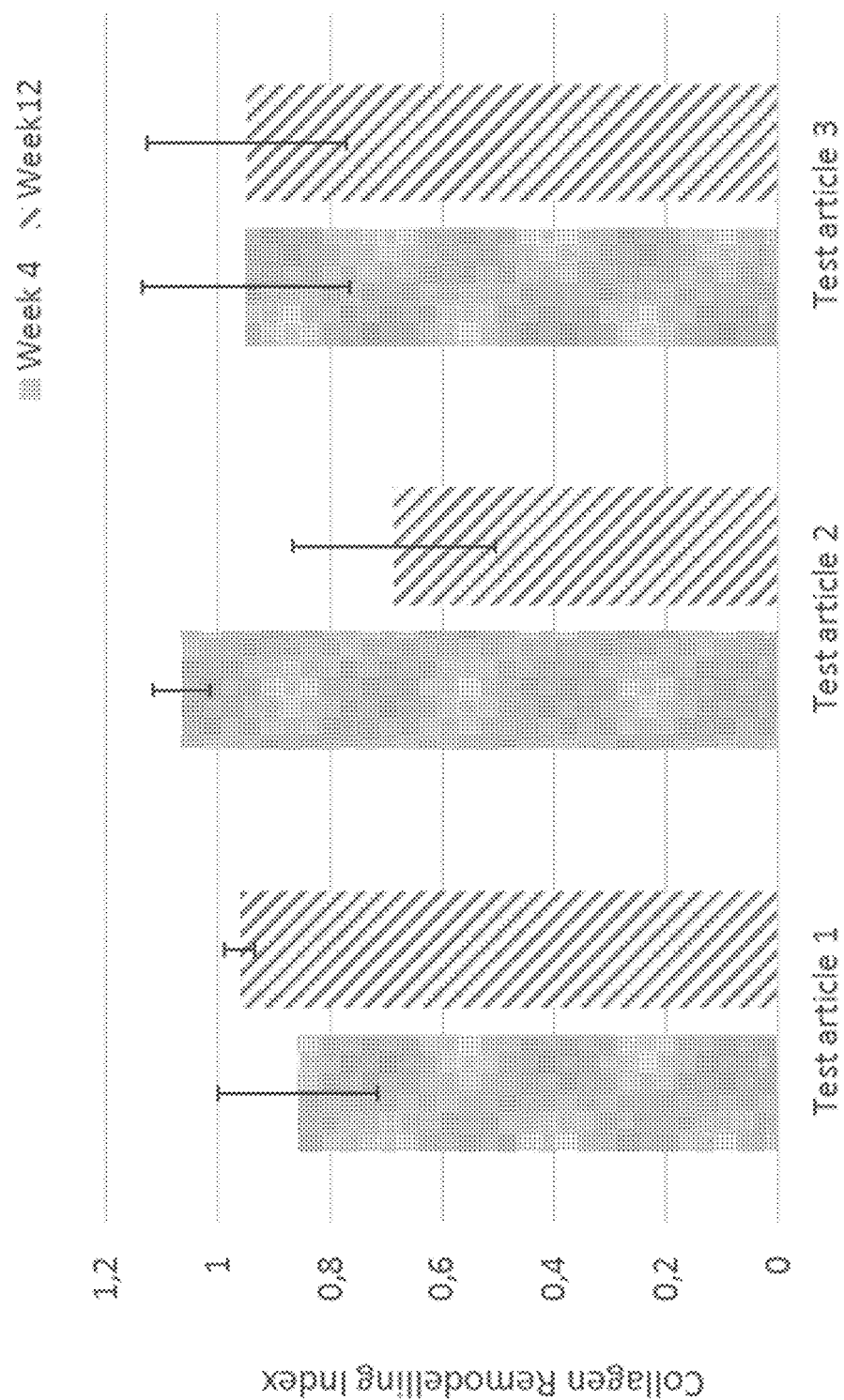
FIG. 4 depicts the quantification of the collagen remodelling index within the implanted area after 4 and 12 weeks of subcutaneous implantation in rabbits. Low, close to 1, CRI values indicate increased maturity and ongoing organization and remodelling of collagen fibers type III to type I.
Figure 5A:
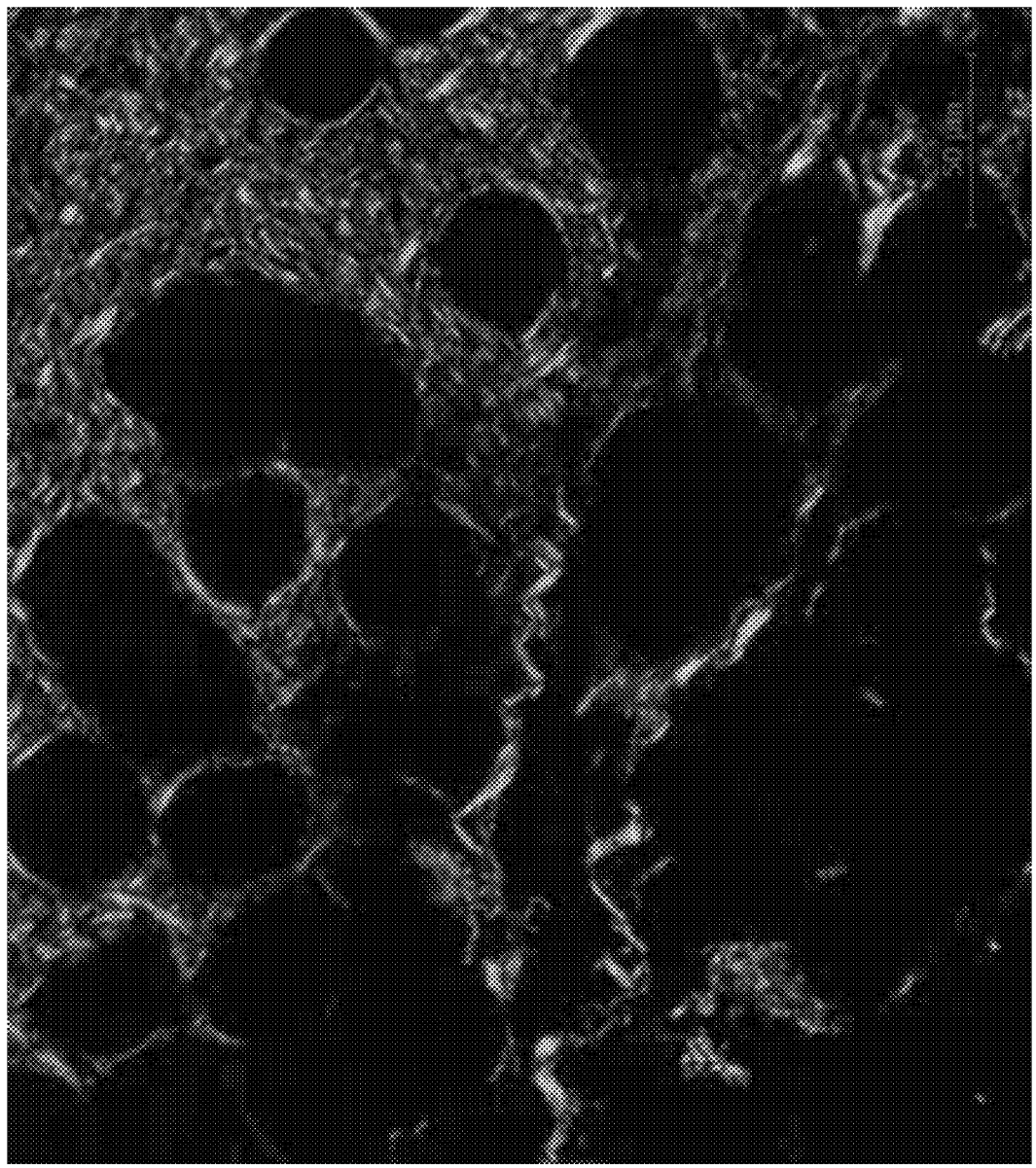
FIG. 5 depicts representative photomicrographs of the evaluation of collagen maturity after 4 weeks (A) and 12 weeks (B) of subcutaneous implantation in rabbits with Test article. Picrosirius red stained sections were analysed under polarized light. Collagen colour indicates increasing maturity and fiber thickness from green to red-orange.
Figure 5B:
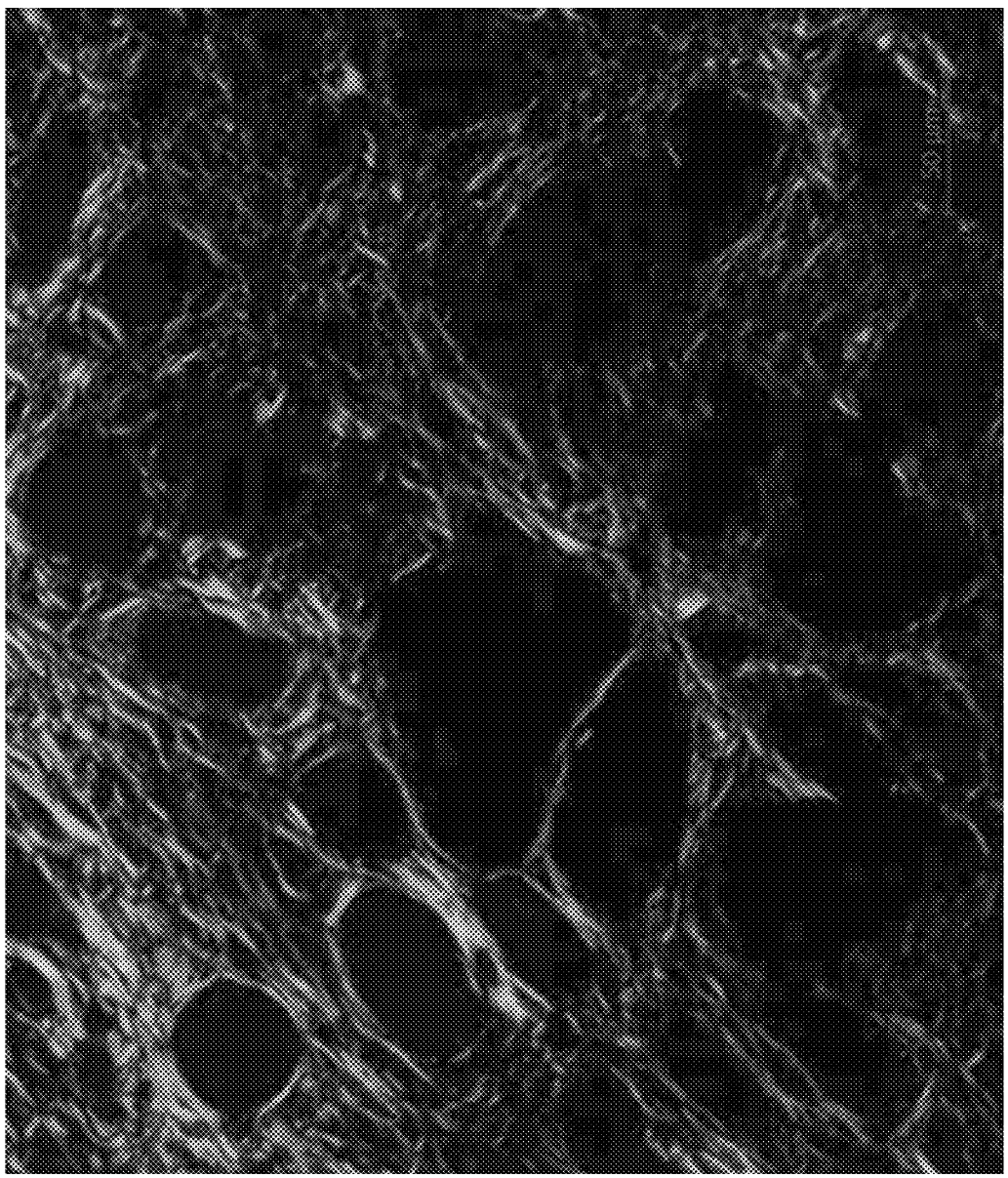

Using cross-polarization microscopy, digitized picrosirius red-stained sections of the Test articles were examined to determine maturity of the collagen present within the implanted area at 4 and 12 weeks of implantation. Under polarized light, collagen fiber colour indicates increasing fiber thickness and maturity from green to red-orange. Accordingly, the ratio of the green (immature, type III collagen) to the red-orange (mature, type I collagen) surface areas within the selected ROI was calculated and is presented as CRI. Results are summarized in FIG. 4, and representative photomicrographs are shown in FIG. 5.

After 4 weeks, CRI values for Test articles 1, 2 and 3 were 0.86, 1.06, and 0.95, respectively which indicates that fibers with a similar birefringence were observed, i.e. there was not a distinct difference in collagen maturity and fiber thickness within the implanted area. After 12 weeks, at least for Test article 2 the analysis of polarized light images showed an increase in the amount of red-orange collagen fibers suggesting that the remodelling, organization and deposition of thick mature type 1 collagen fibers was initiated.

Degradation of Test Article 4 (Gel-Carrier)

At the end of each time-period, the amount of gel-carrier was quantified through histomorphometric evaluation of the surface area of a given ROI on the SHE sections in comparison to the corresponding T0 sites.

Figure 7A:
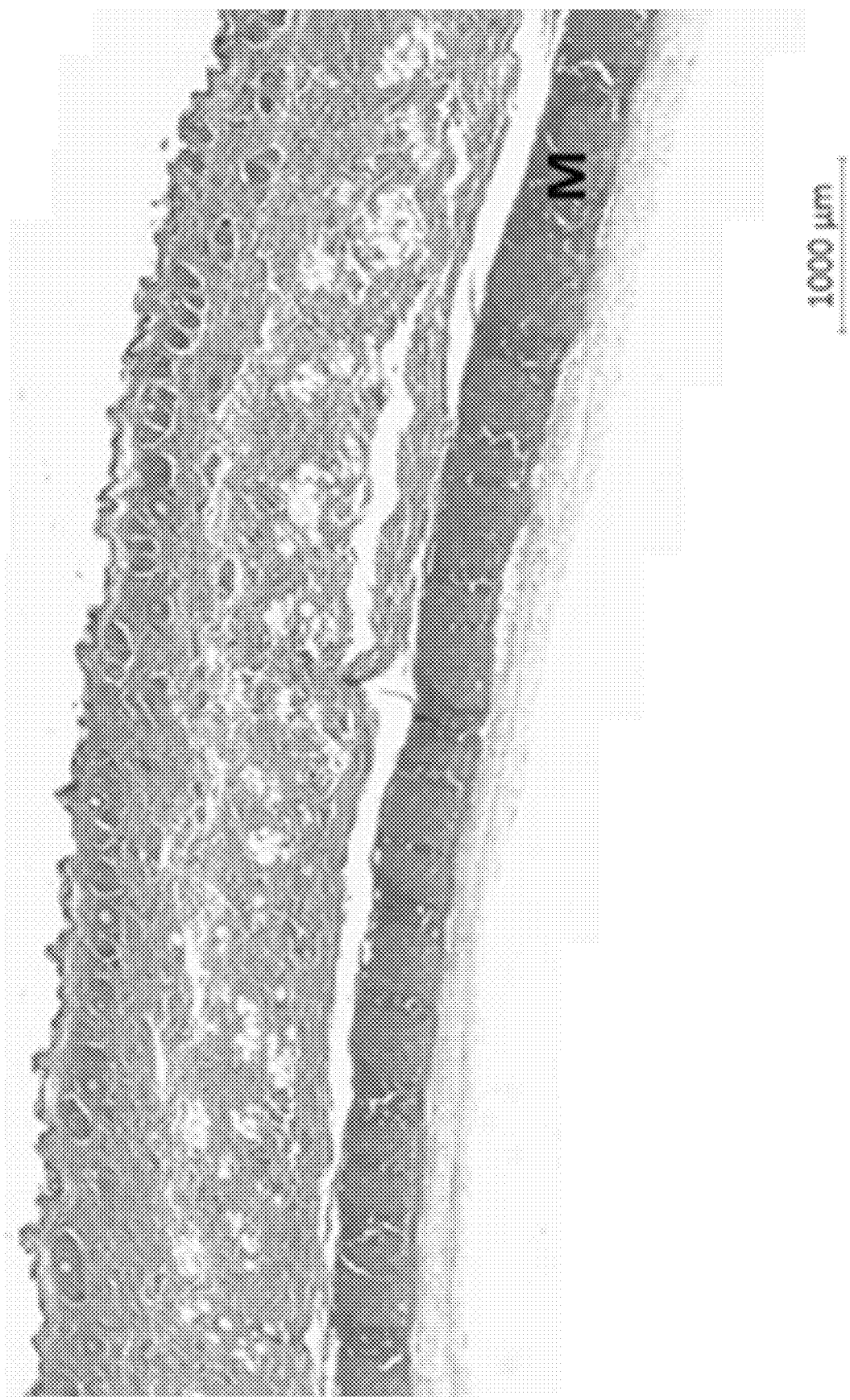
FIG. 7 depicts representative photomicrographs of Test article 4 (gel-carrier) after 4 weeks (A) and 12 weeks (B) of subcutaneous implantation in rabbits. Safranin-hematoxylin-eosin was used for the staining of the histological sections. Complete degradation of the gel carrier is observed after 4 weeks of implantation. M: cutaneous muscle.
Figure 7B:
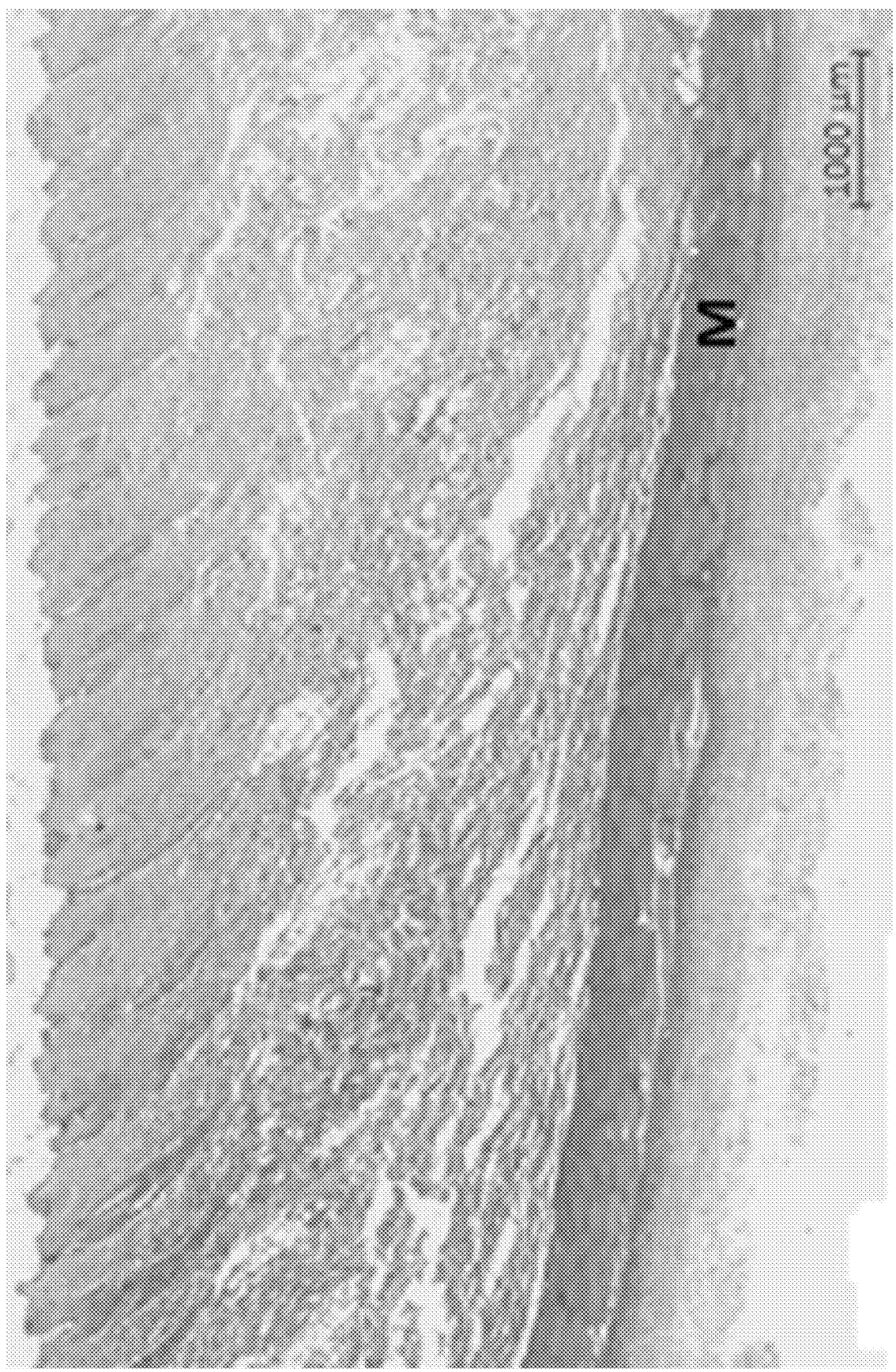

Results showed after four weeks of subcutaneous implantation in the back of rabbits, the gel-carrier was already fully degraded. Accordingly, no product was detected after 12 weeks of implantation (FIG. 6, representative photomicrographs in FIG. 7).

Histopathologic Evaluation—Local Tissue Effects:

Histopathologic evaluation of the local tissue effects including the inflammatory response at the injection sites was conducted in adaptation to the standard (ISO 10993-6) on the SHE and Alcian blue sections.

Overtime following subcutaneous injection in the rabbit, the test articles 1 to 3 showed slight to moderate signs of degradation without inducing local side effects. The grade of local inflammation observed with the test articles 1 to 3 (moderate) was associated with the presence of the polymer microspheres, as the carrier material (test article 4), fully degraded, generated only a slight residual local inflammation. When compared to the test articles 1 to 3, comparator 1 and 2 elicited lower signs of local inflammation.

Macroscopic observations of the implant sites revealed no signs of edema, erythema or eschar for any articles from Day 0 to Week 12.

CONCLUSION

This study aimed to investigate the neocollagenesis potential of PTMC microspheres suspended in a CMC gel-carrier in comparison to currently marketed HA-based dermal filler products, following subcutaneous administration in an animal model.

Results demonstrate that the PTMC microsphere composition according to the invention triggers a foreign body reaction in the local tissue characterized by higher stimulation of de novo synthesis and deposition of native collagen when compared to HA-based comparator products, resulting in up to a two-fold higher amount of synthesized collagen already at 4 weeks post implantation. Moreover, the ratio of immature (type III) collagen to mature, stable collagen (type I) was shown to shift over time in favour of the mature type I collagen, indicative of a structural restoration of the extracellular matrix network with the reconstitution of collagen molecules into their native fibrillar structure.

The invention claimed is:

1. An in vivo resorbable composition comprising a poly (1,3-trimethylene carbonate) polymer (PTMC) and a resorbable gel carrier, wherein the gel carrier is in the form of an aqueous polysaccharide gel, wherein the PTMC is in the form of microparticles with a diameter ranged between 1 and 200 µm, and wherein the microparticles have homogenous content and density throughout the microparticle, are essentially round and have smooth surfaces.

2. The in vivo resorbable composition according to claim 1, wherein the gel carrier comprises the viscoelastic feature of shear thinning.

3. The in vivo resorbable composition according to claim 1, wherein the gel carrier comprises a polysaccharide selected from the group consisting of a cellulose-derivative polysaccharide, a starch, a chitin, a chitosan, a hyaluronic acid, a hydrophobically modified polysaccharide, an alginate, a carrageenan, an agar, an agarose, an intramolecular complex of a polysaccharide, an oligosaccharide and a macrocyclic polysaccharide.

4. The in vivo resorbable composition according to claim 3, wherein the polysaccharide gel carrier comprises a cellulose-derivative polysaccharide.

5. The in vivo resorbable composition according to claim 1, wherein the PTMC is a homopolymer, a linear polymer, a branched polymer, a copolymer, a terpolymer, a blend or composite of different types of homo/co/ter-polymers, or a crosslinked polymer.

6. The in vivo resorbable composition according to claim 1, wherein the PTMC has a number average molecular weight (Mn) of about 500 to about 600,000 g/mol.

7. The in vivo resorbable composition according to claim 1, wherein the PTMC is present in a concentration of about 1 to about 40 volume percent (v/v) by weight of the composition.

8. The in vivo resorbable composition according to claim 1, wherein the gel carrier material is present in a concentration of about 0.2 to about 20 weight percent (w/w) by weight of the composition.

9. The in vivo resorbable composition according to claim 1, wherein the composition has a viscosity of about 5,000 to about 5,000,000 mPa·s at room temperature.

10. The in vivo resorbable composition according to claim 1, wherein a further substance is present.

11. The in vivo resorbable composition according to claim 1, wherein the composition is a pharmaceutical composition.

12. The in vivo resorbable composition according to claim 1, wherein the composition is a cosmetic or esthetic composition.

13. The in vivo resorbable composition according to claim 1, wherein the composition is a composition for augmenting tissue.

14. A method of treating a skin abnormality or disfigurement, controlling bladder function, controlling gastric reflux, treating erectile dysfunction and/or premature ejaculation, treating vocal cords, and/or treating joint and cartilage diseases comprising administration of an in vivo resorbable composition according claim 1.

15. The in vivo resorbable composition according to claim 4, wherein the cellulose-derivative polysaccharide, is selected from the group consisting of carboxymethylcellulose, ethylcellulose, microcrystalline cellulose and oxidized cellulose.

16. The in vivo resorbable composition according to claim 15, the resorbable polysaccharide gel carrier comprises sodium carboxymethlycellulose.

17. The in vivo resorbable composition according to claim 6, wherein the PTMC has a number average molecular weight (Mn) of about 100,000 to about 600,000 g/mol.

18. The in vivo resorbable composition according to claim 10, wherein the further substance is an active ingredient.

19. The in vivo resorbable composition according to claim 18, wherein the active ingredient is an anesthetic.

20. The in vivo resorbable composition according to claim 1, wherein the composition is a composition for augmenting soft tissue.

21. The in vivo resorbable composition according to claim 1, wherein the composition is an implant or filler for intradermal, deep-dermal, subdermal or subcutaneous use.

* * * * *